United States Patent [19]
Fabian et al.

[11] Patent Number: 6,025,171
[45] Date of Patent: Feb. 15, 2000

[54] IMMOBILIZING ENZYMES AND PROCESSING TRIGLYCERIDES WITH IMMOBILIZED LIPASE

[75] Inventors: Jurgen Fabian; Johan Paul Geurtsen; Martin Roger Grote; Karel Petrus Van Putte; Adrianus Rozendaal, all of Vlaardingen, Netherlands

[73] Assignee: Lipton, Division of Conopco, Inc., Englewood Cliffs, N.J.

[21] Appl. No.: 08/991,307

[22] Filed: Dec. 16, 1997

[30] Foreign Application Priority Data

Dec. 19, 1996 [EP] European Pat. Off. .............. 96203644

[51] Int. Cl.⁷ .............................. C12P 7/64; C12N 11/10; C12N 11/08; C12N 9/20
[52] U.S. Cl. .......................... 435/134; 435/178; 435/179; 435/180; 435/198
[58] Field of Search .................................... 435/134, 174, 435/177, 178, 179, 180, 198

[56] References Cited

U.S. PATENT DOCUMENTS

| | | | |
|---|---|---|---|
| 5,182,201 | 1/1993 | Tsuda ...................................... | 435/176 |
| 5,330,905 | 7/1994 | Kula et al. .............................. | 435/183 |

FOREIGN PATENT DOCUMENTS

| | | |
|---|---|---|
| 0035883 | 9/1981 | European Pat. Off. . |
| 140542 | 5/1985 | European Pat. Off. . |
| 0320132 | 6/1989 | European Pat. Off. . |
| 0356240 | 2/1990 | European Pat. Off. . |
| 382767 | 8/1990 | European Pat. Off. . |
| 0407058 | 1/1991 | European Pat. Off. . |
| 444092 | 9/1991 | European Pat. Off. . |
| 0513709 | 11/1992 | European Pat. Off. . |
| 05344897 | 12/1993 | Japan . |
| 2159527 | 12/1985 | United Kingdom . |
| 89/01032 | 2/1989 | WIPO . |
| 95/22606 | 8/1995 | WIPO . |
| 97/01632 | 1/1997 | WIPO . |

*Primary Examiner*—David M. Naff
*Attorney, Agent, or Firm*—Matthew Boxer

[57] ABSTRACT

Enzymes are immobilized by preparing an emulsion containing a continuous hydrophobic phase such as a triglyceride oil and a dispersed aqueous phase containing an amphiphilic enzyme such as lipase or phospholipase and carrier material that is partly dissolved and partly undissolved in the aqueous phase, and removing water from the aqueous phase until the phase turns into solid enzyme coated carrier particles. The undissolved part of the carrier material may be a material that is insoluble in water and oil, or a water soluble material in undissolved form because the aqueous phase is already saturated with the water soluble material. The aqueous phase may be formed with a crude lipase fermentation liquid containing fermentation residues and biomass that can serve as carrier materials. Immobilized lipase is useful for ester re-arrangement and de-acidification in oils. After a reaction, the immobilized enzyme can be regenerated for a subsequent reaction by adding water to obtain partial dissolution of the carrier, and with the resultant enzyme and carrier-containing aqueous phase dispersed in a hydrophobic phase evaporating water to again form enzyme coated carrier particles.

13 Claims, 2 Drawing Sheets

IMMOBILIZING ENZYMES AND PROCESSING TRIGLYCERIDES WITH IMMOBILIZED LIPASE

The present invention relates to a process for the immobilization of enzymes and the use of the immobilized enzymes for catalyzing the processing of triglyceride fats.

BACKGROUND OF THE INVENTION

Enzymes are used on an industrial scale as catalysts for processing various crude materials. Often these processes are cost-effective only when the enzymes can be re-used many times. For recirculation the enzymes need to be separated from the process liquid. This is possible when the enzymes are attached to a carrier which can be filtrated or centrifuged.

An important group of industrial enzymes have an amphiphilic nature. These enzymes are characterized by the presence of a hydrophilic part as well as a hydrophobic part in the molecule. Lipases and phospholipases are representatives of this group of enzymes. Amphiphilic enzymes are enzymes which, when dispersed in an oil and water emulsion, will migrate and accumulate in the interface of the aqueous phase and the oil phase. This is the definition of amphiphilic enzymes in the context of the present invention. The hydrophobic part of the enzyme points into the hydrophobic phase and the hydrophilic part points into the aqueous phase.

The invention will be described with lipase as most important example of an amphiphilic enzyme. Other industrially applied amphiphilic enzymes are phospholipases of which various types are known and which are e.g. used for the hydrolysis of phospholipids to lysophospholipids.

Lipases are employed for their ability to modify the structure and composition of triglyceride oils and fats. They catalyze different types of triglyceride conversions, such as hydrolysis, esterification and transesterification. These are equilibrium reactions which in one direction result into hydrolysis of triglycerides into free fatty acids and glycerol, mono- or diglycerides, and in the other direction result into re-esterification of glycerol, monoglycerides and diglycerides into triglycerides. For the re-esterification process removal of the water which is formed in the reaction medium is necessary to shift the equilibrium in the direction of triglyceride synthesis.

The use of lipase in a substantially water-free process medium needs the dispersion of lipase in oil in an active form, which is a major problem. For that purpose preferably an immobilized lipase is used which is active in an oil which contains a slight amount of dissolved water but not any dispersed water.

Presently the main process for immobilized lipase manufacture comprises first a microbiological fermentation of suitable microorganisms which produce the enzyme under proper conditions, a removal of the micro-organisms and an optional enzyme purification. Then a solution of the obtained lipase is added to a carrier and the enzyme is allowed to get attached to the carrier surface. Such immobilization method is exemplified for an interesterification process in e.g. GB 2 159 527. The attachment of the enzyme to the carrier enables easy separation of the irreversibly immobilized enzyme from the process medium for subsequent use.

Generally, the used carrier materials are porous, particulate, water insoluble materials which provide large surface areas per unit volume are. The preparation of immobilized enzymes is described in e.g. EP 0 140 542, EP 0 382 767, WO 95/22606, EP 0 444 092 and WO 89/01032.

During the enzymatic triglyceride processing the immobilized enzyme gradually looses its activity. It has to be substituted frequently by a fresh enzyme preparation. The enzyme consumption determines for a major part the total processing costs. A great economy advantage would be obtained, when it would be possible to extend the lifetime of the enzyme.

In the usual porous carrier materials mass transfer limitations further decrease the lipase activity.

Our earlier not pre-published patent application WO 97/01632 describes a process for immobilizing an enzyme in a cheap and easy way as well as a process for re-generating and re-activating such enzyme preparation when after use it eventually has become worn-out. The first process comprises the steps a. selecting an amphiphilic enzyme for immobilization, b. preparing an emulsion comprising a continuous hydrophobic phase and a dispersed aqueous phase in which aqueous phase are dissolved the enzyme and material suitable to act as carrier for the enzyme when the next step is carried out, c. removing water from the dispersed phase until this phase turns into solid enzyme coated particles.

In said application the carrier material is described as material fully soluble in the aqueous phase. No reference is made of any matter in the aqueous phase which is insoluble.

SUMMARY OF THE INVENTION

The present invention provides a process which comprises the steps a. selecting an amphiphilic enzyme for immobilization, b. preparing an emulsion comprising a continuous hydrophobic phase and a dispersed aqueous phase in which aqueous phase are dissolved the enzyme and material suitable to act as carrier for the enzyme when the next step is carried out, c. removing water from the dispersed phase until this phase turns into solid enzyme coated particles, where the aqueous phase additionally contains undissolved material.

The invention also provides processes in which the obtained immobilized enzyme is employed.

DETAILS OF THE INVENTION

Figure 1:
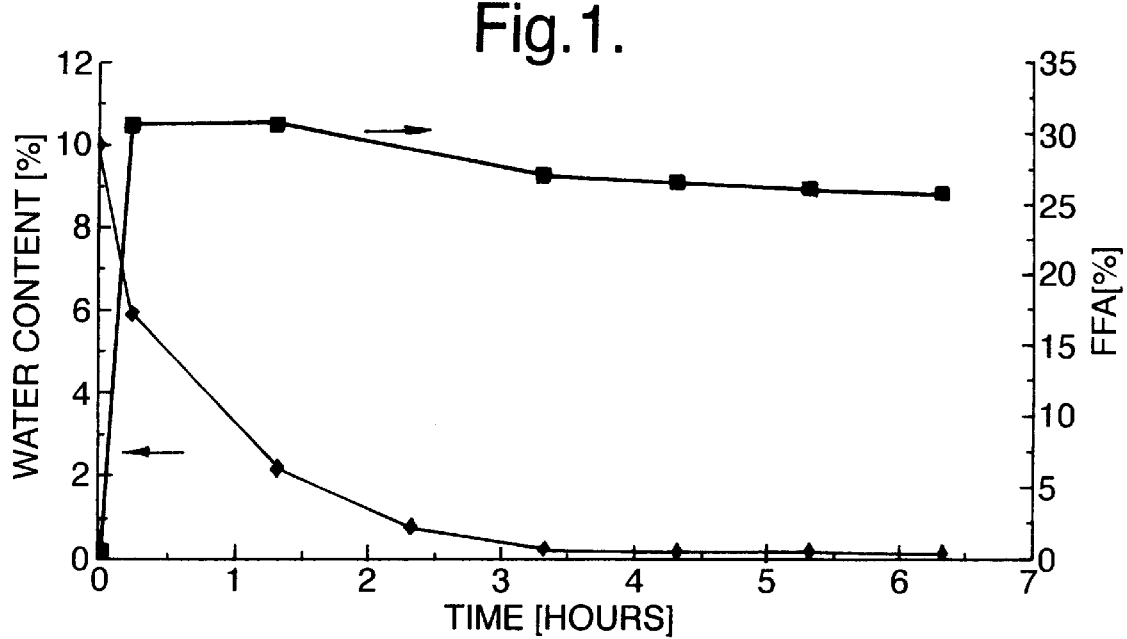
FIG. 1 shows how the water content and the free fatty acids content change during an in-situ enzyme immobilization process according to the present invention.

The starting emulsion is prepared with, preferably, 5–15 wt. %, more preferably 8–10 wt. % of aqueous phase, which is dispersed in the hydrophobic phase. The aqueous phase should contain the amphiphilic enzyme to be immobilized and further both dissolved and undissolved material both of which which can act as carrier after water has been evaporated from the aqueous phase droplets as described below.

The water soluble carrier material is selected preferably from the group consisting of sugars, such as sucrose, lactose and glucose, starch, such as wheaten flour, dextran, water soluble cellulose derivatives and fermentation residues.

The not dissolved part of the carrier material may consist of material which is neither soluble in water, nor in oil. Alternatively, it may consist of material which as such is soluble in an aqueous phase but which in the actual case is present in undissolved form because it is dispersed in an aqueous phase which is already saturated with such water-soluble material. Consequently, when the temperature is varied, the dissolved amount of such material will vary too.

Materials which as such are not soluble are suitably chosen from the group consisting of biomass, cereal grains and insoluble soybean components. Also, generally, inert grains of natural or synthetic material such as porous polypropylene particles.

Biomass is understood to comprise the inactivated water insoluble remains of micro-organisms used in a fermentation process.

Carrier material, when not or not sufficiently present in the aqueous phase, is added to the aqueous phase before or after the aqueous phase is dispersed into the hydrophobic continuous phase.

The amount of carrier material is preferably chosen such that enough carrier surface is available for the enzyme to get attached. Large particles are favoured for easy separation, but they have a smaller surface/weight ratio than small particles. Generally the carrier material is used in an amount of 0.5–5 wt. % on oil, preferably 1–2 wt. %.

Fermentation residues are understood to be all substances still present in a fermentation liquid after fermentation and which are contained in the supernatant after the water insoluble biomass has been separated from the fermentation liquid. Optionally, this supernatant is concentrated, e.g. by passing it through a crossflow hollow fibre microfiltration membrane module (known as artificial kidney). Fermentation residues comprise polysaccharides, proteinaceous material, salts and sugars. These substances are dissolved in the aqueous fermentation liquid but will separate as solid, particulate matter when the water is removed. According to a specific embodiment fermentation residues are used together with any proper biomass which will act as the insoluble part of the carrier.

Other insoluble carrier material can be added additionally.

The content of insoluble carrier material may vary widely, e.g. from 0.001–99 wt. % of the total carrier material, preferably, 0.01–80 wt. % and, more preferably, 0.1–20 wt. %. The range may vary depending on the carrier material or combination of carrier materials. Suitable compositions can easily be established by those skilled in the art.

The enzyme containing aqueous phase is dispersed as fine droplets in the hydrophobic phase by usual emulsifying techniques. According to its nature the amphiphilic enzyme migrates to and accumulates in the interface of aqueous phase and hydrophobic phase.

Any lipase suitable for triglyceride hydrolysis or re-esterification may be used, but preferably, a lipase is used which is obtained from *Rhizomucor miehei*, *Humicola lanuginosa* or *Rhizopus niveus* fermentation. The amount of added enzyme activity is adapted to the particular process for which it is intended. Generally, a suitable lipase activity is 100–1500 lipase units (LU) per gram of oil. One lipase unit (LU) is defined as the amount of enzyme which liberates one micromole butyric acid per minute from an emulsified tributyrin substrate (at pH 7.0 and 30° C.).

The hydrophobic phase of the emulsion may be any food-grade liquid in which the aqueous phase can be dispersed, which preferably is an edible triglyceride oil and which acts as the enzyme substrate. If the hydrophobic phase is not the substrate, this should be added separately. Alternatively, the immobilized enzyme particles are separated from the system in which they have been prepared and collected for future use which comprises addition to a substrate oil. Preferably, the hydrophobic phase consists of a triglycerides mixture, which optionally further contains diglycerides, monoglycerides, glycerol and fatty acids.

If a triglyceride oil is used for immobilization, preferably an oil is chosen which is substantially phospholipids free, otherwise the phospholipids may adversely interfere with the formation of the enzyme coated particles. Preferably the triglyceride oil contains not more than 100 ppm of hydratable phospholipids. Consequently, when the aim of the enzymatic process is the hydrolysis of phospholipids, the immobilized enzyme particles have to be prepared in a separate system which is phospholipids free.

Common standard techniques are available for the necessary removal of water from the emulsion, including the addition of molecular sieves and conducting an inert gas, such as nitrogen, through the emulsion. Drying is best accomplished by gradual evaporation of water, preferably at 30° C.–35C., applying a vacuum of preferably 1–100 mbar, more preferably 3–20 mbar. Optionally, a combination of such measures is used.

When the water gradually disappears from the dispersed aqueous phase, the droplets shrink and get desiccated. In the same time dissolved material will separate as solid particulate matter. The enzyme, which initially is accumulated in the W/O interface, will eventually deposit on and get attached to solid particulate matter which has been formed in the shrinking desiccated droplet. Depending on the amount of enzyme available in the aqueous phase the carrier particles will be coated fully or partially with an enzyme layer. In this way desiccation of the dispersed phase provides an in-situ immobilized enzyme preparation. The enzyme when immobilized may be used immediately, provided its substrate is made available in the hydrophobic phase, or the immobilized enzyme may be separated and added to a substrate oil or stored for future use.

In the beginning of the immobilization proces a lipase containing W/O-emulsion is formed and glyceride molecules, when present, start to be hydrolyzed into fatty acids and diglycerides, monoglycerides and glycerol. The hydrolysis is continued until a pre-chosen level is attained. But as soon as water is removed from the process mixture, the enzymatic ester hydrolysis turns into an enzymatic re-esterification process. However, some lipases are known to be not capable of effectively re-esterifying hydrolysed glycerides. This is apparent from a hardly declining fatty acids level (see FIG. 1).

The immobilization process preferably is carried out at a temperature of 30° C.–35° C.

The immobilized lipase has an increased temperature stability, provided the enzyme acts in a non-aqueous environment which lacks any dispersed water. However, the water dissolved in the triglyceride oil to be processed should be sufficient for the initial hydrolysis step. Depending on the type of lipase, processing temperatures of 60° C. or even 70° C. are allowed. With this robust enzyme systems it is possible to process hardstock fats, even when having melting points in the range of 40° C.–60° C., a range which is beyond the maximum processing temperature of most aqueous lipase preparations.

The immobilized enzymes according to the invention may be employed in batch-wise processing as well as in continuous mode processing. The size of the solid enzyme coated particles should be large enough for allowing separation, e.g by centrifugation, filtration or decanting. Because of ease of separation the size is at least 0.1 $\mu$m, preferably at least 1 $\mu$m and more preferably 5–25 $\mu$m. Since with increasing size the surface available for enzyme attachment (per weight unit) is decreasing, a proper balance should be made.

A particular advantage of the present invention is that the invention does not need a pure enzyme. Time consuming and expensive procedures for recovery and purification of the enzyme from the crude fermentation liquid can be dispensed with, when desired, since e.g. fermentation residues and biomass provide suitable carrier materials.

The invention further comprises processes catalyzed by an immobilized amphiphilic enzyme according to the invention. To such processes belong lipase catalyzed ester rearrangements and also acidolysis in which triglycerides are reacting with fatty acids.

Ester rearrangement processes may involve mono-, di- or triglycerides, in which, under the catalytic action of a lipase, fatty acid groups are exchanged among the glycerol backbones of the triglyceride molecules.

The enzymatic de-acidification of a triglyceride oil involves the catalytic action of a lipase where fatty acids are removed by esterification with mono- or diglycerides also present in the oil.

Enzymes in-situ immobilized according to the invention, when separated from a reaction batch either by filtration, decantation or centrifugation, can be re-used many more times.

For a rearrangement process the immobilized lipase preparation is added as such to a triglyceride oil batch. No water needs to be added, provided sufficient water for the initial hydrolysis step is present in dissolved form in the triglyceride oil to be processed. Although only 0.3 wt. % of water dissolves in oil at ambient temperatures, it is enough for a smooth enzyme reaction.

The immobilized enzyme is economically used for a series of at least two subsequent enzyme catalyzed reactions, where in the reactions series at least once an enzyme activity regeneration step is included.

Such regeneration or reactivation process may comprise dispersing water into an immobilized-enzyme-in-oil system, allowing the enzyme and its carrier to interact with the water resulting into partial dissolution of the carrier material and thereafter evaporating the water of the dispersed phase so that enzyme coated carrier particles are formed again.

For said reactivation preferably 5–15 wt. %, more preferably 8–10 wt. % of water phase is added and dispersed into the hydrophobic phase. The dissolved enzyme migrates to and accumulates in the water/oil interface. When the water is removed, as described before, the droplets by desiccation shrink and dissolved carrier material again separates as solid matter. When the water is progressively disappearing from the desiccating droplets, the enzyme will finally adhere again to the carrier.

Alternatively, the used enzyme-on-carrier is first separated, from the reaction batch, admixed with a water phase with the effect that the enzyme and a part of the carrier dissolve, whereafter the obtained water phase is dispersed in an oil phase and desiccated as described before.

Optionally, the enzyme-on-carrier after been separated is added to a ready W/O-emulsion for being subjected to a reactivation treatment.

The re-immobilization results in a restoration, at least partially, of enzyme activity. The effect of restoration may be noted as a stabilization of activity or a decrease of the usual and expected inactivation.

Figure 2:
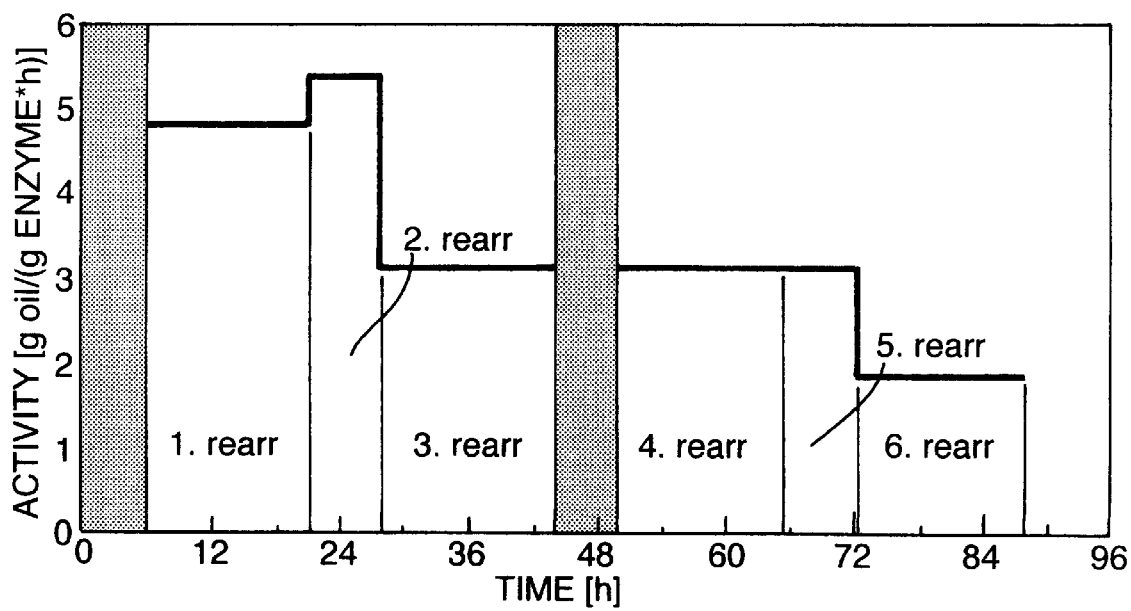
FIG. 2 shows the activity of a lipase enzyme immobilized according to the invention in the course of several subsequent rearrangement processes interrupted by a single re-immobilization treatment (dark-shaded area) after about 48 hrs.
Figure 3:
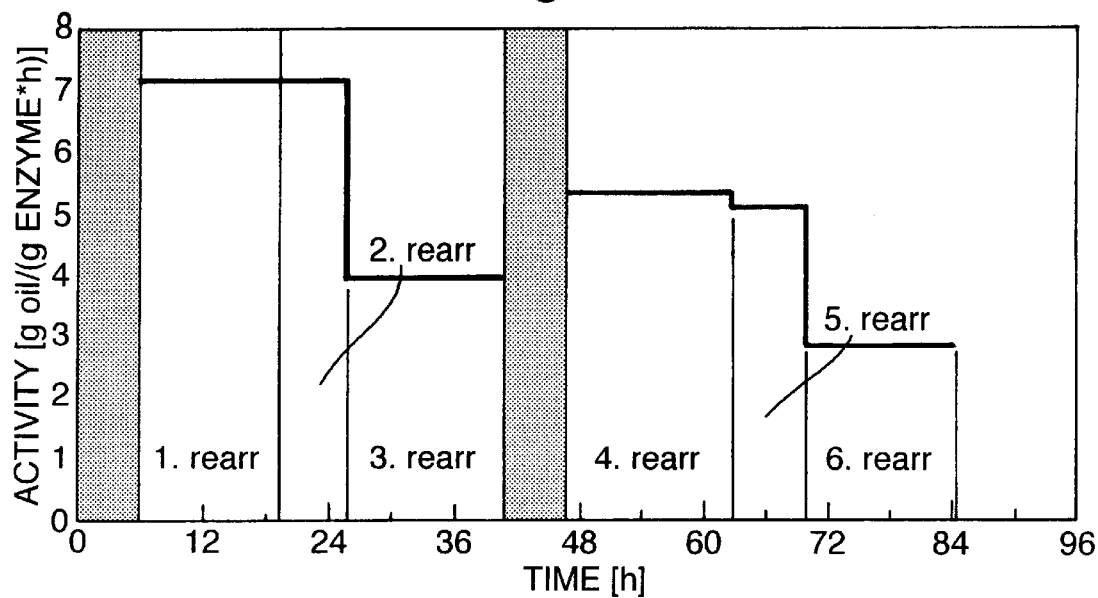
FIG. 3, see FIG. 2, but a different carrier system has been used for immobilization.
Figure 4:
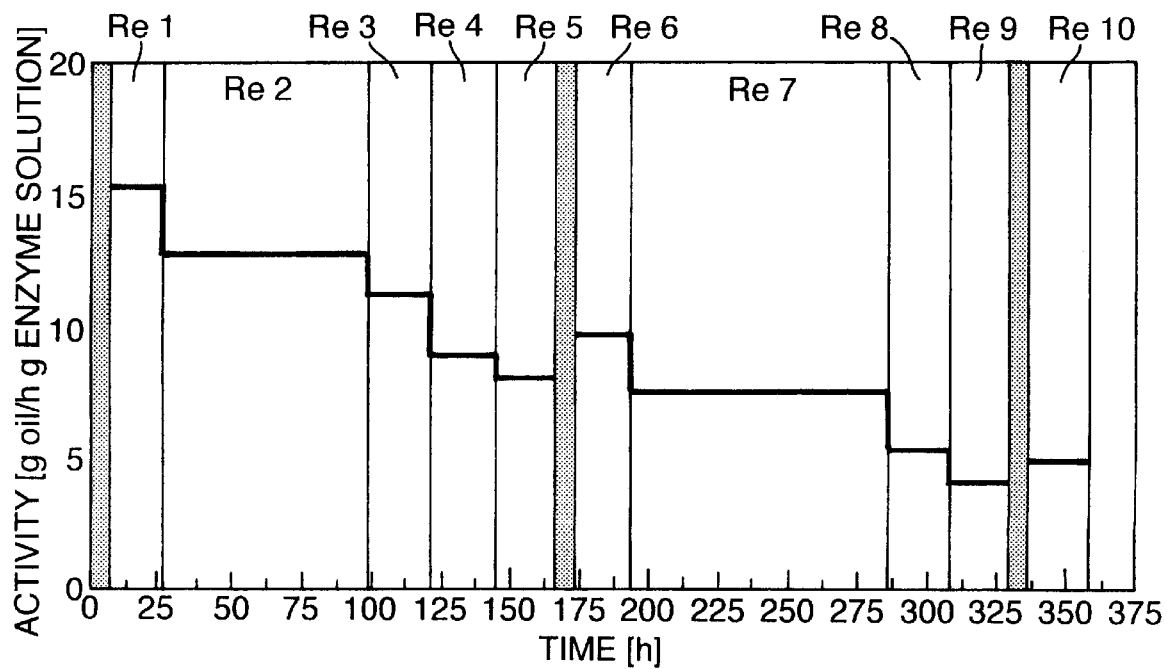
FIG. 4, see FIG. 2, but a different carrier system has been used for immobilization. Two re-immobilization treatments have been applied.

The re-activation by re-immobilisation may be repeated again and again and provides a prolonged use of enzyme and carrier substance. FIGS. 2, 3 and 4 show the re-use of an immobilized lipase enzyme in consecutive batches. The gradual decrease of enzyme activity in subsequent rearrangement steps is partially mended (FIGS. 3 and 4) or at least stopped (FIG. 2) by re-immobilization (marked by dark shaded areas) using the same enzyme and the same carrier material. Optionally, enzyme damaged or spent during the process is compensated by adding some fresh enzyme preparation.

The activity and stability of the immobilized enzyme may be pH dependent. The pH should be adjusted before the (re-)immobilization is carried out. Suitable pH's may be found in the range of 5–8, depending on enzyme and carrier.

The ongoing re-use of materials, the cheap preparation of enzyme starting from a non-purified form and the absence of expensive carrier material greatly economizes on costs of expensive catalyst. Moreover waste problems related to the disposal of spent enzyme material are reduced. Such advantageous features are unique and not described for enzymes immobilized according to prior art processes.

The invention is illustrated by the following examples:

GENERAL

In order to monitor the progress of the process in the following examples, oil samples were taken at time intervals. Samples taken from the reaction medium with a needle were admixed with anhydrous sodium sulphate in order to remove remaining water from the oil and then heated above 85° C. in a 2 ml glass sample tube in order to deactivate the enzymes.

Free fatty acid content was determined by dissolving about 0.5 g of homogenised oil in 50 ml of a neutral solvent, comprising equal volumes of ethanol (96%) and diethyl ether (p.a.) and titrating it with a 0.1 mole/l sodium hydroxide solution, using phenolphtalein as indicator. The free fatty acid (FFA) content follows from:

$$\% \, FFA = \frac{V.M.}{W.} \frac{282}{1000} \cdot 100\%$$

where:

V=titrated volume (ml)

W=weight of the oil sample (g)

M=molarity of the NaOH solution

282=typical molecular weight of fatty acids (in casu oleic acid).

The catalyst activity follows from the following equations:

$$k = -ln(1-x) * M/W.t$$

where:

k: catalyst activity (g oil/g catalyst per h)
M: oil mass (g)
W: mass of catalyst (g enzyme preparation)
t: time (h)
x: degree of conversion defined as $$x = \frac{\sum CN_t - \sum CN_i}{\sum CN_e - \sum CN_i}$$

ΣICN represents the sum of the values of a range of carbon numbers selected for the specific process where the subscripts (t, i, e) refer to the composition at any moment in time (t), to the initial composition (i) and to the equilibrium composition (e), respectively. The carbon number values are obtained by Gas Liquid Chromatography (GLC) sample analysis. For the SF/MCT blend rearrangement the values of CN's 34–46 are selected and for a POs/PKs blend rearrangement the values of CN's 44–46 for calculating the degree of conversion.

EXAMPLE 1

FIG. 1 shows the content of water and free fatty acids during the in-situ immobilization of lipase obtained from *Humicola lanuginosa*. An aqueous yeast extract containing about 0.1 wt. %. of water-insoluble matter was used as a carrier material while sunflower oil (SF) was the continuous oil phase. Free fatty acids were produced because of the water in the process medium. The hydrolysis stopped when by applying vacuum water was removed from the system.

In a reactor, provided with a stirrer, 10 kg of water were mixed with 2 kg of powdered yeast extract (ex OHLY, Germany) which acted as carrier material and 1 kg of liquid enzyme solution (ex NOVO, Denmark), which was prepared from a *Humicola lanuginosa* fermentation liquid and which contained 100k NOVO lipase units per gram of solution. A separate batch reactor, provided with a stirrer and a water jacket, was filled with 100 kg of sunflower oil (SF) and heated to a temperature of 35° C. The enzyme-carrier-mix was filled into the oil after thorough mixing to ensure a homogeneous situation. Vigorous stirring produced a W/O-emulsion with finely dispersed water droplets having a large oil and water interface.

The hydrolysis of the triglyceride molecules started after the aqueous phase addition and was continued at 35° C. until the 30% FFA level was attained.

By lowering the pressure to 5 mbar water was evaporated causing the lipase to be deposited and immobilized on the dried carrier material. Together with the removal of water the production of FFA is stopped and partial re-esterification started. FIG. 1 shows the percentage of free fatty acids and water present in the system over time. Water removal was continued until the water content in the oil has dropped to below the solubility level, which actually was below 0.2%.

This preparation yielded enzyme which was immobilized on the carrier material. Such immobilized enzyme can be separated from the oil and used or re-used for re-arrangement reactions for the production of valuable edible oils. The oil which was used for immobilization can be re-used for the same purpose.

EXAMPLE 2

FIG. 2 shows the enzymatic activity (gram converted oil per gram enzyme per hour) as a function of time (hours) for lipase obtained from *Humicola lanuginosa* and utilized in a subsequent series of rearrangement batches. The dark shaded areas in the graph indicate the in-situ preparation and re-activation respectively of the immobilized enzyme. The temperature of the in-situ immobilization and re-activation process was 35° C. The rearrangement process itself took place at 60° C. The immobilized enzyme preparation was separated from the oil by centrifugation for use in a subsequent process.

The preparation of the batch for the in-situ immobilization process was in principle carried out as described in example 1 and as illustrated by FIG. 1. This time the carrier material utilized was (1.39 wt. %) whole wheat bran which is a natural byproduct of wheat grain processing. It contains about 60 wt. % of water-insoluble matter which eventually results into 0.84 wt. % of solids in the process oil. A batch reactor, provided with a stirrer and a water jacket, was filled with an rearrangement mixture of 127.2 g of medium chain triglycerides (MCT) and 238.95 g of sunflower oil (SF). 95 wt. % of the fatty acids of the MCT were C8–C10 fatty acids and 5 wt. % other acids.

Consecutive rearrangements were carried out for reaction periods some of which were approximately 16 hours (overnight) and some were 8 hours.

FIG. 2 clearly exhibits the change of average activity per batch over time during the various rearrangements of the SF/MCT oil mixture. In this particular case the deactivation between rearrangements Re1 and Re3 (direct comparison is allowed since process duration is equal) is 36%. The re-generation after the third rearrangement step resulted in an only slightly higher activity. But without regeneration a further drop in activity would have occurred.

EXAMPLE 3

FIG. 3 shows how immobilized lipase obtained from *Humicola lanuginosa* was utilized in a subsequent series of rearrangement batches. The activity (gram converted oil per gram enzyme per hour) is shown as a function of time (hours). As carrier materials were utilized deactivated fermentation residues and porous polypropylene particles. The dark shaded areas in the graph indicate the in-situ preparation and re-activation respectively of the enzyme preparation. The temperature of the in-situ immobilization and re-activation process was 35° C., while the rearrangement process took place at 60° C. Before use in a subsequent process the immobilized enzyme preparation was separated from the oil by centrifugation and filtration.

For the in-situ immobilization the batch was prepared and the process in principle applied as described in example 1 and illustrated by FIG. 1. The utilized carrier materials were 5.1 g of deactivated fermentation residues from a *Rhizopus niveus* fermentation and dissolved in 30.9 g of water and 1.8 g of porous polypropylene particles (Accurel™, ex AKZO, the Netherlands). A batch reactor, provided with a stirrer and a water jacket, was filled with a mixture of 127.2 g of medium chain triglycerides (MCT) and 238.95 g of sunflower oil (SF) for rearrangement. 95% of the fatty acids of the MCT were C8–C10 fatty acids and 5% were other acids.

FIG. 3 clearly exhibits the change of average enzyme activity over time during the rearrangement of the SF/MCT oil mixture. In this particular case the initial enzyme activity of rearrangements Re1 dropped from a value of 100% to a level of 54.7% in rearrangement Re3. Direct comparison is allowed since process duration is equal. The re-generation after the third rearrangement step resulted in an activity increase to 73.9% of the initial level. Without regeneration a further activity drop of the initial level was expected.

EXAMPLE 4

FIG. 4 shows the enzymatic activity (gram converted oil per gram enzyme per hour) as a function of time (hours) for lipase obtained from *Humicola lanuginosa* and utilized in a subsequent series of rearrangement (Re) batches. The dark shaded areas in the graph indicate the in-situ preparation and re-activation respectively of the immobilized enzyme. The temperature of the in-situ immobilization and re-activation process was 35° C. The rearrangement process itself took place at 60° C. The immobilized enzyme preparation was separated from the oil by centrifugation for use in a subsequent process.

The preparation of the batch for the in-situ immobilization process was in principle carried out as described in example 1 and as illustrated by FIG. 1. The catalyst was dispersed and dissolved in an aqueous solution. The pH was adjusted at 7 when the immobilization was carried out and again at the begin of the second regeneration. At the begin of the first regeneration the pH was adjusted at 6.3. This time the utilized carrier material was yeast extract containing about 0.1 wt. % of water insoluble matter and less than 1 wt. % of salt.

A batch reactor, provided with a stirrer and a water jacket, was filled with a rearrangement mixture of 127.2 g of medium chain triglycerides (MCT) and 238.95 g of sunflower oil (SF). 95 wt. % of the fatty acids of the MCT were C8–C10 fatty acids and 5 wt. % other acids.

Eight consecutive rearrangements were carried out for reaction periods of 22–23 hours each and for two reaction periods of 73 and 93 hours (over the weekend). Reactivation treatments had been inserted after rearrangements Re5 and Re9.

FIG. 4 clearly exhibits the change of average activity per batch over time during the various rearrangements of the SF/MCT oil mixture. In this particular case the enzyme activity in rearrangement Re1 having an initial value of 100% dropped to a value of 53% in rearrangement Re5. Direct comparison is allowed since process duration is equal.

The re-generation after the fifth rearrangement step resulted in an activity increase to 64% of initial value. But without regeneration a further drop in activity to a level of 39%–47% would have occurred, just like the drop after rearrangement steps Re3 and Re4.

At the ninth rearrangement the enzyme activity has dropped to 26.8% of initial value, but regeneration thereafter resulted in an increase to 32.7% of initial value.

What is claimed is:

1. A process for the immobilization of an enzyme, comprising the steps:
   a. selecting an amphiphilic enzyme for immobilization,
   b. preparing an emulsion comprising a continuous hydrophobic phase and a dispersed aqueous phase which aqueous phase contains the enzyme and a carrier material suitable to act as a carrier for the enzyme when the next step is carried out, said carrier material being partly dissolved and partly undissolved in the aqueous phase, and the undissolved carrier material being from 0.1 to 99 wt. % of the total dissolved and undissolved carrier material, and
   c. removing water from the dispersed aqueous phase until this phase turns into solid enzyme coated particles.

2. A process according to claim 1, wherein the enzyme is selected from the group consisting of lipases and phospholipases.

3. A process according to claim 2, wherein the lipase is obtained from *Rhizomucor miehei, Humicola lanuginosa* or *Rhizopus niveus* fermentation.

4. A process according to claim 1, wherein the aqueous phase comprises a fermentation liquid.

5. A process according to claim 1, wherein the hydrophobic phase is an edible triglyceride oil.

6. A process according to claim 1, wherein the dissolved carrier material is selected from the group consisting of sugars, starch, dextran, water soluble cellulose derivatives and fermentation residues.

7. A process according to claim 1, wherein the undissolved carrier material consists either of material which is neither soluble in water, nor in oil or of material which is soluble in the aqueous phase but which is present in undissolved form due to the aqueous phase being saturated with the dissolved carrier material.

8. A process according to claim 1, wherein the hydrophobic phase contains a substance to be processed, and said substance is one or more of those selected from the group consisting of triglycerides, diglycerides, monoglycerides, glycerol and fatty acids.

9. A process of catalyzing the processing of triglyceride fats with an amphiphilic enzyme, wherein the enzyme is an immobilized enzyme obtained according to claim 1.

10. A process comprising a successive series of at least two lipase catalyzed reactions which reactions are processes according to claim 9, and wherein after a lipase reaction catalyzed there is an enzyme activity regeneration step which regeneration step comprises adding water to the immobilized enzyme, allowing the enzyme and its carrier to interact with the water, dispersing the carrier and enzyme that has interacted with water into an oil phase and evaporating the water from the aqueous phase to form enzyme coated carrier particles again ready for use in the next lipase catalyzed reaction.

11. A process for the ester re-arrangement of mono-, di- or triglycerides, in which, under the catalytic action of a lipase, fatty acid groups are exchanged on a glycerol backbone, wherein the lipase is immobilized according to claim 1.

12. A process for the enzymatic de-acidification of a triglyceride oil, in which under the catalytic action of a lipase, fatty acids are esterified with mono- or diglycerides, wherein the lipase is immobilized according to claim 1.

13. A process catalyzed by a phospholipase, wherein the phospholipase is immobilized according to claim 1.

* * * * *